United States Patent [19]

Benjamin, Jr. et al.

[11] 4,077,402
[45] Mar. 7, 1978

[54] APPARATUS FOR PROMOTING BLOOD CIRCULATION

[76] Inventors: J. Malvern Benjamin, Jr.; D. Ridgely Bolgiano; Carl R. McHenry, all of c/o Bionic Instruments, Inc., 221 Rock Hill Road, Bala Cynwyd, Pa. 19004

[21] Appl. No.: 699,699

[22] Filed: Jun. 25, 1976

[51] Int. Cl.² ............................................. A61H 1/00
[52] U.S. Cl. ................................... 128/24 R; 128/64
[58] Field of Search ............... 128/24 R, 44, 64, 24.1, 128/24.2, 297–302

[56] References Cited

U.S. PATENT DOCUMENTS

| | | | |
|---|---|---|---|
| 2,690,174 | 9/1954 | Fuchs | 128/44 |
| 2,893,382 | 7/1959 | Demeny | 128/64 |
| 3,303,841 | 2/1967 | Dennis | 128/24 R |
| 3,835,845 | 9/1974 | Maher | 128/64 |

*Primary Examiner*—Lawrence W. Trapp
*Attorney, Agent, or Firm*—Smith, Harding, Earley & Follmer

[57] ABSTRACT

Apparatus for promoting blood circulation in a body part suffering from a circulation deficiency by inflating and deflating a pressure cuff applied to a patient's limb proximal to the affected body part so that the blood is forced into the affected body part. The apparatus is synchronized with the patient's heartbeat by way of an EKG pickup and automatically compensates for the blood transit time from the heart to the point of cuff application. The apparatus includes control means responsive to the sensing of the blood flow at a location distal to the cuff for achieving optimum blood circulation in the body part being treated.

10 Claims, 2 Drawing Figures

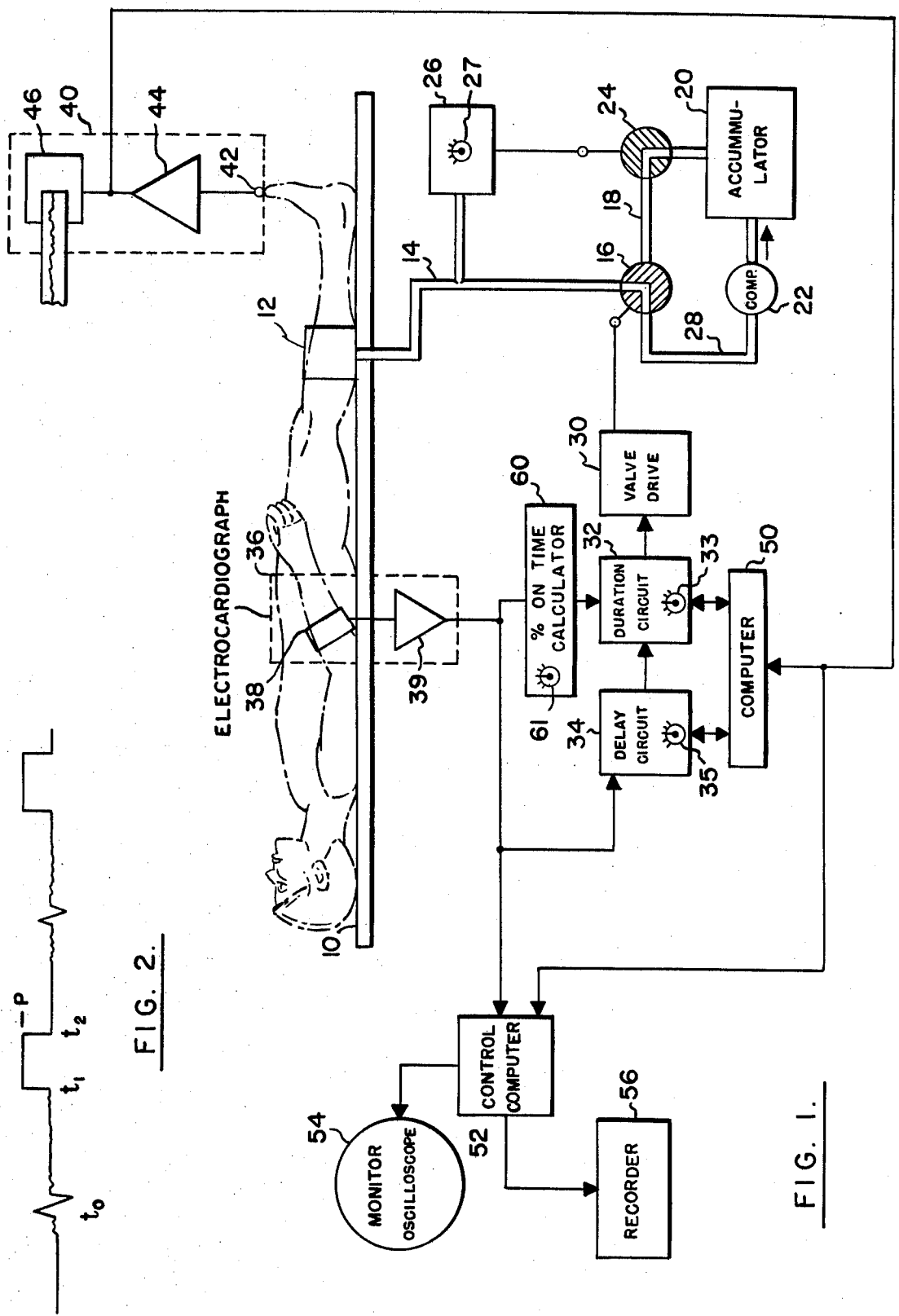

4,077,402

APPARATUS FOR PROMOTING BLOOD CIRCULATION

BACKGROUND OF THE INVENTION

There has been provided an instrument developed by a Swiss physician, Dr. Maurice Fuchs, sold under the name "Syncardon" during the late 1940's, and described in U.S. Pat. No. 2,690,174. This instrument operated to increase circulation in a body part by augmenting arterial pulsatile blood flow thereof. For example, to increase blood flow in the foot a pneumatic cuff is placed around the thigh or calf and is inflated rhythmically in synchronism with the heartbeat by apparatus as described in the patent. The above-described instrument never achieved acceptance or commercial success. This was due, in large part, to the fact that the electronics and pneumatics of the instrument were sufficiently unreliable that considerable expertise was required to keep the apparatus in operation and the fact that the operator had no way of actually monitoring the increased blood flow in the affected part.

In the past ten years, somewhat similar devices have been built containing a balloon that is lodged in the aorta (invasive) or containing cuffs placed around body parts (non-invasive). Such a device is known as a "counterpulsation balloon pump" and has the object of reducing the load on the heart by adding an additional externally-powered pump to the action of the heart itself to thereby take some of the strain from the heart.

Accordingly, the state of the art is that there is no satisfactory device for the treatment of body areas suffering from circulation deficiency by promoting blood flow in these body areas.

SUMMARY OF THE INVENTION

It is the general object of the present invention to provide an apparatus for promoting blood circulation in a body part having a circulation deficiency which apparatus achieves the desired results by monitoring the blood flow and adjusting the parameters of the apparatus to maximize this flow.

The apparatus in accordance with the present invention promotes blood circulation by inflating and deflating a pressure cuff which is applied to a limb proximal to a body part with poor circulation so that it will force blood into the affected body part. The apparatus comprises means for synchronizing the cuff inflation with the heartbeat of the patient by way of an EKG pickup and automatically compensates for the blood transit time from the heart to the point of cuff application. The apparatus also sets automatically the time during which the cuff is inflated to produce optimum results. Also, means are provided for rapidly inflating and deflating the cuff. Means are provided for setting the time during which the cuff is inflated as a proportion of the pulse rate. The apparatus in accordance with the invention includes a blood flow transducer which is placed distal to the cuff and is used as a feedback device for controlling the inflation of the cuff.

In addition, the apparatus in accordance with the invention provides a recording of the patient's blood flow before treatment, during treatment and following treatment, as well as a recording of the various controlling parameters of the instrument and an indication of the treatment time.

BRIEF DESCRIPTION OF THE DRAWING

FIG. 1 is a schematic illustration of the apparatus in accordance with the invention; and FIG. 2 is a view of a typical recording of the various controlling parameters of the apparatus of FIG. 1.

DETAILED DESCRIPTION OF THE PREFERRED EMBODIMENT OF THE INVENTION

The apparatus in accordance with the invention is shown schematically on the block diagram in FIG. 1 of the drawings. The apparatus is illustrated in this figure in association with a patient who is shown lying on a treatment table 10 for the treatment of an ulcer on the lower right leg, for example. As will appear more fully hereafter, the patient is electrically connected to the apparatus by way of electrocardiograph electrodes, the patient is mechanically connected by way of a probe of a blood flow measuring instrument which optically picks up his blood pulse from a toe and the patient is pneumatically connected to the apparatus by way of a cuff placed around his calf.

The apparatus comprises means for applying pressure to the selected body part of the patient. Such means comprises a pressure cuff 12, the specific construction of which will depend upon the body part on which it is to be placed. The cuff 12 is an inflatable, elastic hollow cylindrical means having an elastic inner wall and a more rigid outer wall. The cuff is preferably provided with overlapping "Velcro" fastening strips for attaching the cuff to the body and may take a form similar to the well-known blood pressure measuring devices in use today.

The apparatus is provided with means for supplying air under pressure to the cuff 12. Such means comprises a conduit 14 which is connected to the interior of the cuff 12. The other end of conduit 14 is connected to a port of a solenoid-operated three-way valve 16. A positive pressure is supplied to another port of valve 16 by way of a conduit 18 from an accumulator tank 20 supplied with air under pressure by an air compressor pump 22. Typically, compressor pump 22 maintains a pressure of 40 Psig. in the accumulator tank 20. A normally-closed solenoid-operated valve 24 is connected in the conduit 18 to control the flow therethrough. Valve 24 is actuated between open and closed positions by a pressure transducer 26 which senses the pressure in line 14 (which pressure is the same as the pressure in the cuff 12) and controls the energization of the solenoid for the valve 24. The solenoid of valve 16 operates to actuate it between the position shown in FIG. 1 and a position providing communication between conduit 18 and conduit 14 in which position air under pressure is supplied to the cuff from the accumulator 20 when valve 24 is in its normally-closed position.

Means are also provided for supplying a vacuum, or negative pressure, to the cuff 12. Such means comprises a vacuum source which includes the air compressor pump 22 and a conduit 28 arranged to connect the suction of the compressor pump 22 to a port of the three-way valve 16 as shown in FIG. 1. With the valve 16 in the position shown in FIG. 1, conduit 28 is in flow communication with conduit 14 through valve 16 and the suction of the compressor pump 22 is connected to the interior of the cuff 12 and operates to evacuate the same rapidly.

The pneumatic system shown in FIG. 1 will be provided with appropriate safety valves, check valves and mufflers as in conventional in the art, such devices being eliminated from FIG. 1 for the sake of clarity of illustration.

The pneumatic system operates as follows:

At the time of initiation of a cycle, the cuff 12 is in a deflated condition so that the pressure transducer 26 senses zero pressure and its normally closed switch is closed to thereby actuate valve 24 to the position shown in FIG. 1. This connects the air under pressure from the accumulator 20 to a port of valve 16. Since valve 16 (as shown) is presently in the vacuum position, it shuts off the pressure arriving through valve 24. The cycle beings with the initiation of a QRS complex from the electrocardiograph at time $t_0$ shown on FIG. 2. This starts a delay circuit which times out at time $t_1$ at which time valve 16 is actuated to the position interconnecting conduits 14 and 18. Air at 40 Psig. pressure is applied to the cuff 12 through valves 24 and 16 in series. The pressure transducer 26 allows this process to continue until the cuff 12 has achieved a pressure ("P" on FIG. 2) which opens the pressure transducer switch, thus actuating valve 24 to the closed position and maintaining the cuff pressure "P" as preset at the pressure transducer 26 by a suitable control dial 27.

Meanwhile, the electronic circuit which timed out the delay period also started a duration circuit at the same time as it actuated valve 16. The duration times out at time $t_2$ whereupon valve 16 is restored to its original "vacuum" position, thus rapidly exhausting the cuff 12. As the cuff 12 exhausts, the pressure transducer 26 senses that the pressure is too low and once again actuates valve 24 to the open position putting pressure at the port of valve 16 ready for the next cycle. Valve 16 cuts off the pressure at this point since it is in the "vacuum" position shown in FIG. 1.

In the "Syncardon" prior art instrument, the cuff was inflated from a pressure source controlled by a regulator valve set by the physician to the maximum pressure that he wished the cuff to achieve. The cuff would then be inflated by opening an inflation valve. At the end of the duration period, another valve would be opened to atmosphere allowing the cuff to deflate. The effect of the "pulse pumping" action is increased in accordance with the pneumatic system in accordance with the invention because both the rise and fall time of the cuff pumping is shortened. The rise time of the pulse is shortened by the elimination of the regulator valve and by the utilization of an air supply from a high pressure source (the accumulator 20 being at approximately 40 Psig). In order to keep from damaging the patient or the cuff 12, the pressure transducer 26 is connected to sense the cuff pressure and this pressure transduscer in turn controls the valve 24 which controls the filling of the cuff 12. Pressure transducer 26 is provided with a control dial 27 so that it can be set for the desired peak cuff pressure ("P" of FIG. 2) by the physician. It will be apparent that because of the higher inflow pressure provided with the pneumatic system in accordance with the invention, the rise time to achieve the requisite cuff pressure is greatly reduced. Also, the fall time is greatly shortened because the exhaust is connected to a vacuum instead of to atmospheric pressure which, of course, speeds the exhausting action.

In other words the pneumatic system in accordance with the invention comprises a feedback loop in which the cuff pressure is measured and this measured cuff pressure is allowed to determine how long the filling is to continue. This is an improvement over the prior art set up in which the pressure is set to what the cuff is to be filled. Accordingly, the rise time curve has a much sharper slope in the pneumatic system in accordance with the invention as compared with the slope of the curve for the Syncardon instrument. A further advantage of the pneumatic system in accordance with the invention is that for a much greater portion of the allowable period the system operates at high pressure so that you get the maximum influence of driving the blood downward.

Means are provided for controlling the inflation of the cuff by controlling the application of air to the cuff from the pressure supply. Such means comprises a valve drive 30 for actuating the valve 16 between its flow-controlling positions, namely, a first or "pressure" position in which the valve provides communication between the positive pressure supply conduit 18 and the conduit 14, and a second or "vacuum" position in which the valve 16 provides communication between the vacuum supply conduit 28 and the conduit 14. The control means also comprises a duration circuit 32 which determines the time period during which the valve drive 30 holds the valve 16 in the "pressure" position. Connected to the duration circuit 32 is a delay circuit 34 which initiates operation of the duration circuit 32 at a predetermined time after the patient's heartbeat. Both the delay circuit 34 and the duration circuit 32 are of conventional design.

The delay circuit 34 and the duration circuit 32 are operated in response to various conditions of the patient and the apparatus in accordance with the invention comprises means for sensing these conditions. To this end, there is provided an electrocardiograph 36 comprising electrode means 38 which includes a pair of electrodes attached to the patient's arm and which sends its output through an EKG amplifier 39 connected by suitable electrical lines to the delay circuit 34. There is also provided a blood flow measuring instrument 40 (such as the one sold under the trademark "Hemorheograph" by Bionic Instrments, Inc.) which has a probe 42 attached to the toe of the patient or some other location whereat the flow is directly related to the blood flow in an effected body part. The probe 42 optically senses the blood flow and provides an electrical output signal having an amplitude and wave shape corresponding to the blood flow being sensed. The output signal of the probe 42 is connected to the amplifier 44 of the blood flow measuring instrument 40, the output of which is connected to a computer 50 by suitable electrical lines as shown on FIG. 1. The signal from the amplifier 44 is also delivered to a chart recorder 46 which makes a record of the blood flow sensed.

As shown in FIG. 1, the outputs from the EKG amplifier 39 and the Hemorheograph amplifier 44 are connected to a control computer 52. The control computer 52 is provided with a suitable selector switch for connecting to a monitor oscilloscope 54 either the electrocardiograph or the blood flow signals. This permits the operator of the instrument to view the various functions thereof on the monitor oscilloscope 54.

The control computer 52 is also provided with a selector switch for sending the electrocardiograph and blood flow pulse signals to a recorder 56. Under the control of the control computer 52, the recorder 56 can be operated to make a recording of the patient's blood flow before treatment, during treatment and following treatment, as well as a recording of the various control parameters of the instrument and an indication of the treatment time. The provision of the recorder means permits the maximal use of the apparatus in accordance with the invention. It has been determined that two treatments a day lasting a half an hour to an hour per treatment for a period of 10 days minimum are required to produce a permanent improvement in circulation. For such treatments to be given under a doctor's care, either the patient must be hospitalized or a doctor or medical technician's time must be taken up for frequent and extended periods. By providing suitable means for recording the performance of the apparatus and the reaction of the patient, it is possible to avoid the need for additional medical or paramedical personnel to be with the patient at all times. With a patient of normal intelligence, it is only necessary for the medical doctor to set up the apparatus initially, instruct the patient in its use and, from time to time, look at the recordings and monitor the patient's condition.

Means are provided for automatically setting the time period during which the cuff 12 is inflated in order to produce the maximum blood flow in the region being sensed by the Hemorheograph probe 42, which corresponds to the blood flow in the body part being treated. To this end, a computer 50 is interconnected with the delay circuit 34 and the duration circuit 32 for registering the action of these circuits and is provided with means for altering the timing of both such circuits by a small amount after each cycle of operation in the following manner.

In succeeding cycles of operation, the computer 50 sequentially alters the timing of either the delay circuit 34 or the duration circuit 32 a small amount in one direction. The computer 50 registers the results during each succeeding cycle of operation. If the previous alteration of the timing of the delay circuit 34 or duration circuit 32 results in an increase in the output from the Hemorheograph amplifier 44, the next computer alteration is in the same direction. If, on the other hand, the prior alteration results in a decrease in the output from the Hemorheograph amplifier 44, the next alteration is in the opposite direction. In this manner, after several cycles of operation, wherein the computer has been alternately adjusting the delay circuit and the duration circuit, the delay circuit 34 and the duration circuit 32 are finally set to produce optimum results, namely, the maximum blood flow in the region being sensed by the Hemorheograph probe 42.

The computer 50 consists of a microprocessor suitably programmed to run the program described above and there is provided suitable switching means to cut the computer out of the control circuit if desired. This permits the control to be performed either manually or by another control circuit as will appear hereafter.

There is also provided means for setting the duration circuit 32 to be a fixed fraction of the pulse rate. To this end, there is provided a percent on time calculator 60 which is connected to the duration circuit 32 as shown in FIG. 1. The calculator 60 receives the output from the EKG amplifier 39. More specifically, the purpose of the percent on time calculator is to adjust the duration time to be a fixed percentage of the reciprocal of the pulse rate. The circuitry detects each pulse from the electrocardiograph amplifier 39 and from this pulse derives the average rate for five consecutive pulses and takes the reciprocal of this average rate and multiplies it by a constant between 0 and 1 which has been set in the calculator 60 by the operator by means of a setting dial 61. This is accomplished by a conventional analog circuit means or can be software programmed digitally into a section of the computer 52 if desired. The percent on time calculator 60 is provided with an appropriate switch for connecting it into and out of the circuit of the apparatus as desired.

The delay circuit 34 is provided with a control dial 35 for the manual setting of the delay time and the duration circuit 32 is provided with a control dial 33 for the manual setting of the duration time. Accordingly, the computer 50 and the percent on time calculator 60 may be switched electrically out of the system and the delay time and the duration time can be set by the manual adjustment of the control dials 35 and 33, respectively.

The apparatus in accordance with the invention is set up for operation by connecting the various elements to the patient on the table 10 in the manner illustrated in FIG. 1. The Hemorheograph probe 42 is attached distal to the body area to be treated and is therefore distal to the cuff 12, which is applied proximal to the affected area (for example, for treatment of an ulcerated foot, the cuff 12 might be applied to the calf and the probe 42 to the toe). The maximum allowable cuff pressure "P" is set by the physician by setting the control dial 27 of the pressure transducer 26. The pressure setting is to a value that the physician considers physiologically safe based upon his previous experience.

The apparatus is then turned on and the delay and duration settings are set into the apparatus either by means of the computer 50 and the percent on time calculator 60 or by a manual adjustment. When the computer 50 is used, the delay and duration times are set automatically in the manner described in detail above. When the percent on time calculator 60 is used, there is built into the calculator 60, whether it is set manually by the dial 61 or automatically, circuitry which holds the duration always to a fixed percentage of the cardiac cycle in the manner as described above.

In the manual setting of the delay and duration times, the operator observes the pulse amplitude shown by the Hemorheograph recorder 46 and the delay control dial 35 is slowly turned by the operator first in one direction and then in the other until the pulse amplitude has been maximized. The operator then turns his attention to the duration control dial 33 which is manipulated in a similar fashion in order to once again maximize the pulse amplitude appearing on the Hemorheograph recorder 46. The delay control dial 35 is then once again readjusted and the duration once again readjusted and the pulse should then be maximized.

A typical treatment of a patient by the use of the apparatus in accordance with the invention takes the following course:

After the delay time and duration time have been set in the apparatus, the apparatus is allowed to run for approximately half an hour with the recorder 56 turned off. Occasionally, such as every ten minutes in the course of treatment, the recorder 56 is turned on for a period of 15 seconds to document the blood flow during this period. At the end of the period, the apparatus is turned off and the recorder is turned on to document the flow which has by then been achieved. Frequently, at the beginning of a course of treatments the blood flow in the affected part will almost immediately drop to its pretreatment level when the machine has been turned off. However, as these treatments progress it is found that the blood flow in the affected body part remains higher after the treatment.

We claim:

1. Apparatus for promoting blood circulation in a body area of a patient comprising:
   an inflatable cuff means adapted to be attached to a part of the patient for applying pressure to such part upon inflation of the cuff means,
   means for supplying fluid under pressure,
   conduit means interconnected between said pressure supply and said cuff means for transmitting fluid under pressure from said pressure supply to said cuff means,
   means for controlling the flow of fluid through said conduit means for controlling the inflation of said cuff means,
   means for sensing the heartbeat of the patient, and
   means for sensing the blood flow in a part of the patient distal to said cuff means.

2. Apparatus according to claim 1 wherein said control means includes control circuit means responsive to said heartbeat sensing means and said blood flow sensing means for controlling the time and duration of the inflation of said cuff means.

3. Apparatus according to claim 1 including control circuit means responsive to said heartbeat sensing means for synchronizing the time of inflation of said cuff means with the heartbeat of the patient to compensate for the blood transit time from the heart of the patient to the point of cuff application on the patient.

4. Apparatus according to claim 3 including circuit means responsive to said heartbeat sensing means for automatically setting the time period during which the cuff remains inflated as a percentage of the pulse rate.

5. Apparatus according to claim 1 wherein said control means includes valve means controlling flow through said conduit means and a valve drive for actuating said valve means between a pair of flow controlling positions, said fluid pressure supply including means for supplying fluid under a positive pressure condition and means for supplying fluid under a negative pressure condition, means for connecting said positive pressure supply to said valve means, means for connecting said negative pressure supply to said valve means, said valve means being operative to connect said positive pressure supply to said cuff means in one of said flow controlling positions thereof to cause inflation of said cuff means and to connect said negative pressure supply to said cuff means in the other flow controlling position thereof to cause deflation of said cuff means.

6. Apparatus according to claim 2 wherein said control circuit means includes a delay circuit portion and a duration circuit portion, and including an electrocardiograph pickup which is connected to said delay circuit to start the operation thereof, the output of said delay circuit being connected to said duration circuit to start the beginning thereof, and means responsive to said blood flow sensing means and connected to said duration circuit for controlling operation thereof.

7. Apparatus according to claim 1 including recorder means for providing a recording of the heartbeat of the patient and the blood flow at said part distal to said cuff means at desired times during operation of the apparatus.

8. Apparatus for promoting blood circulation in a body area of a patient comprising:
   an inflatable cuff means adapted to be attached to a part of the patient for applying pressure to such part upon inflation of the cuff means,
   means for supplying fluid under pressure,
   conduit means interconnected between said pressure supply and said cuff means for transmitting fluid under pressure from said pressure supply to said cuff means, and
   means for controlling the flow of fluid through said conduit means for controlling the inflation of said cuff means,
   said control means including valve means controlling flow through said conduit means and a valve drive for actuating said valve means between a pair of flow controlling positions,
   said fluid pressure supply including for supplying fluid under a positive pressure condition and means for supplying fluid under a negative pressure condition, and
   means for connecting said positive and said negative pressure supply to said valve means,
   said valve means being operative to connect said positive pressure supply to said cuff means in one of said flow controlling positions thereof to cause inflation of said cuff means and to connect said negative pressure supply to said cuff means in the other flow controlling position thereof to cause deflation of said cuff means.

9. Apparatus according to claim 8 wherein said positive pressure supply includes a source of high pressure fluid and means for sensing the existence of a predetermined pressure in said cuff means for shutting off flow from said source of high pressure to said cuff means.

10. Apparatus according to claim 9 wherein said positive pressure supply includes a compressor and an accummulator receiving the delivery of said compressor for maintaining a supply of high pressure fluid, and said negative pressure supply includes a conduit means connected to the suction of said compressor.

* * * * *